United States Patent [19]

Dustin et al.

[11] Patent Number: 5,071,964
[45] Date of Patent: Dec. 10, 1991

[54] PROTEIN MICELLES

[75] Inventors: Michael Dustin, Boston; Timothy Springer, Chestnut Hill, both of Mass.

[73] Assignee: Dana-Farber Cancer Institute, Inc., Boston, Mass.

[21] Appl. No.: 511,975

[22] Filed: Apr. 17, 1990

Related U.S. Application Data

[63] Continuation of Ser. No. 238,926, Aug. 31, 1988, abandoned, which is a continuation-in-part of Ser. No. 189,971, May 4, 1988, abandoned, which is a continuation-in-part of Ser. No. 19,010, Feb. 26, 1988, abandoned.

[51] Int. Cl.$^5$ .................. A61K 37/10; C07K 13/00
[52] U.S. Cl. ................................ 530/395; 530/352; 530/350; 514/8; 424/88; 424/484
[58] Field of Search .............. 530/350, 352, 395; 514/8; 424/484

[56] References Cited

U.S. PATENT DOCUMENTS 4,578,269 3/1986 Morein .............................. 424/88

OTHER PUBLICATIONS

Sanchez-Madrid, *Proc. Natl. Acad. Sci. USA*, 79, 7489-7493, 1982.

Seed, "An LFA-3 cDNA Encodes a Phospholipid-linked Membrane Protein Homologous to Its Receptor CD2," Nature, 329: 840-842 (1987).

Dustin et al., "Anchoring Mechanisms for LFA-3 Cell Adhesion Glycoprotein at Membrane Surface", Nature, 329 846-848 (1987).

Wallner et al., "Primary Structure of Lymphocyte Function-Associated Antigen 3 (LFA-3) The Ligand of the T Lymphocyte CD2 Glcoprotein," J. of Experimental Medicine, 166: 923-932 (1987).

Caras et al., "Signal for Attachment of a Phospholipid Membrane Anchor in Decay Accelerating Factor," Science, 238: 1280-1283 (1987).

Tiefenthaler et al., "Purified Lymphocyte Function-Associated Antigen-3 and T11 Target Structure Are Active in CD2-Mediated T Cell Stimulation," Eur. J. Immunol. 17:1847-1850 (1987).

Detmers et al., "Aggregation of Complement Receptors on Human Neutrophils in the Absence of Ligand," The J. of Cell Biol., 105: 1137-1145 (1987).

Rosenberry et al., "Structure of Human Erythrocyte Acetylcholinesterase", The J. of Bio. Chem., 259: 5643-5652 (1984).

Hammarström, "Binding of Helix Pomatia A Hemagglutinin to Human Erythrocytes and Their Cells. Influence of Multivalent Interaction on Affinity," Scand. J. Immunol. 2: 53-66 (1973).

O'Flynn et al., "Different Pathways of Human T-Cell Activation Revealed by PHA-P and PHA-M," Immunology, 57: 55-60 (1986).

Hoessli et al., "Association of Specific Cell-Surface Glycoproteins with a Triton X-100-Resistant Complex of Plasma Membrane Proteins Isolated from T-Lymphoma Cells (P 1798), " Experimental Cell Research, 156: 239-250 (1985).

*Primary Examiner*—F. T. Moezie
*Attorney, Agent, or Firm*—Fish & Richardson

[57] ABSTRACT

A micelle of an adhesion protein which naturally includes a phosphatidylinositol lipid anchor, the micelle being capable of binding multivalently to a plurality of target molecules on a cell surface; where the adhesion protein is LFA-3, the LFA-3 micelles can be administered to a patient to inhibit binding of activated T-cells to other cells.

6 Claims, 7 Drawing Sheets

PROTEIN MICELLES

This is a continuation of co-pending application Ser. No. 07/238,926 filed on Aug. 31, 1988 which is a CIP of Ser. No. 07/189,971 field on May 4, 1988 which is a CIP of Ser. No. 07/019,010 filed Feb. 26, 1988; all are now abandoned.

BACKGROUND OF THE INVENTION

This invention relates to adhesion proteins (as defined below), and in particular to lymphocyte function associated antigen-3 (LFA-3), a glycoprotein which is widely distributed on the surfaces of almost all human cells, including monocytes, granulocytes, cytolytic T lymphocytes, B lymphoblastoid cells, platelets, and fibroblasts.

LFA-3 is a ligand for cluster of differentiation 2 (CD2), another glycoprotein, found on the surfaces of T lymphocytes. These two glycoproteins interact to mediate T lymphocyte adhesion to target cells. Similarly, binding of thymocyte to thymic epithelial cells requires CD2 on the thymocyte and LFA-3 on the thymic epithelial cell. LFA 3 in purified form inhibits intercellular adhesion between T lymphocytes and erythrocytes and mediates aggregation of T lymphocytes.

SUMMARY OF THE INVENTION

The invention provides a micelle of an adhesion protein, e.g., LFA-3, which naturally includes a phosphatidylinositol lipid ("PI") anchor; the micelle (which preferably contains less than about ten molecules of the protein) is capable of binding multivalently to a plurality of target molecules on a cell surface. Thus the invention provides multimeric, purified LFA-3 which has an avidity for CD2-bearing cells such that the Kd of the LFA-3 for the cells is lower than the Kd of monomeric LFA-3, which has been determined to be about 400 nM. More preferably, the Kd is <50 nM, and even MORE PREFERABLY <20 Nm. An adhesion protein is defined more preferably <20 nM. herein as any protein mediating the contact and union of two or more human cells, and preferably, is a protein present on the surface of a cell. A target molecule is defined herein as a molecule to which an adhesion protein binds selectively, i.e., binds to a degree greater than the degree to which it binds to any other molecule, preferably, this binding is exclusive.

The micelles of the invention can be used to inhibit the adhesion of a first cell to a second cell where the first cell bears on its surface a PI anchor-bearing protein capable of binding to a molecule present in multiple form on the second cell. The method includes contacting the second cell with a micelle, preferably of less than about 10 such protein molecules (or micelle forming, binding fragments thereof), which is capable of binding multivalently to the multiple molecules on the second cell.

The adhesion protein micelles of the invention can further be used for the treatment of medical conditions characterized by the presence of an excess of activated T-cells by administering LFA-3 micelles in a physiologically compatible buffer to a patient to achieve a bloodstream concentration of LFA-3 effective to inhibit the binding of the activated T-cells to other cells in the patient; the resultant bloodstream concentration of LFA-3 is preferably 0.4 to 40 nM of LFA-3. Disease states characterized by the presence of an excess of activated T-cells include multiple sclerosis, sarcoidosis, juvenile type diabetes mellitus, systemic lupus ery.thmatosis, thyroiditis, rheumatoid arthritis, ankyloses spondylitis, primary biliary cirrhosis, autoimmune hemolytic anemia, immune thrombocytopenia purpura, myesthenia gravis, allograft rejection and graft versus host disease.

Another aspect of the invention features a method of increasing the avidity and decreasing the dissociation constant of any adhesion protein which naturally includes a PI anchor. The method includes solubilizing the adhesion protein in a detergent solution and diluting the detergent below its critical micelle concentration in such a way as to form adhesion protein micelles. A detergent is defined as any small alphipathic molecule having hydrophobic and hydrophilic regions that are preferably spatially separated on the molecule, i.e., one end is charged or polar and the other end is a polar. The critical micelle concentration (CMC) is the concentration of a specific detergent in solution at which micelles just begin to form in the solution. This CMC is different for different detergents.

A further aspect of the invention features a method of effecting activation or proliferation of peripheral blood mononuclear cells or T lymphocytes by contacting such cells with LFA-3 micelles together with an antibody to CD2.

DESCRIPTION OF THE PREFERRED EMBODIMENTS

The drawings will first be briefly described.

DRAWINGS

Purification of LFA-3

The following cell lines were used in research relating to the present invention. Peripheral blood mononuclear cells (PBMC) were isolated by dextran sedimentation and Ficoll-Hypague (Sigma, St. Louis, Mo.) density gradient centrifugation. Peripheral blood T lymphocytes (PBL-T) were enriched by nylon wool (Polyscience, Warrington, Pa.) filtration and plastic adherence. The Jurkat cell line was obtained from Dr. M. K. Ho (Dupont, Boston, Mass.). Cells were maintained in RPMI-1640, 10% fetal bovine serum (Gibco, Grand Island, N.Y.), 5 mM L-glutamine, 50 μg/ml gentamycin (Complete media). JY B lymphoblastoid cells and Jurkat cells for LFA-3 and CD2 purification, respectively, were grown by the MIT Cell Culture Center (Cambridge, Mass.).

LFA-3 was purified from Triton X-100 lysates of human erythrocytes (Dustin, M. L., et al., J. Exp. Med., 65:677 (1987)), or JY B lymphoblastoid cells (Wallner, B. P., et al., J. Exp. Med., 166:923 (1987)), or from supernatants of phosphatidylinositol-specific phospholipase C (PIPLC) treated JY B lymphoblastoid cells by immunoaffinity chromatography on TS2/9 MAb-Sepharose CL-4B (Pharmacia, Piscataway, N.J.). In the latter case, 50 g of viable JY cells were washed with Hank's buffered saline solution (HBSS) and treated with *Bacillus thuringiensis* PIPLC (from Dr. Martin Low, Columbia University, NY, N.Y.) in a total volume of 100 ml for 1 hr. at 37° C. The concentration of enzyme used could hydrolyze 300 nmol/min /ml of $^3$H phosphatidylinositol at pH 7 in the presence of 0.1 % deoxycholate detergent (Low, M.G., Methods Enzymol., 71:741 (1981)). The cells were pelleted at 1000×g and cell debris was pelleted at 10,000×g for 1 hr. Lysates or supernatants containing LFA-3 were passed over the affinity column and the column washed (Dustin, M.L., et al., supra). LFA-3 from erythrocytes was eluted from the immunoaffinity column at pH 3 in the presence of 1% octylglucoside (OG) detergent. LFA-3 from PIPLC supernatants was eluted at pH 3 in the absence of detergent, fractions containing LFA-3 were pooled (4–6 ml), passed over a 1 ml phenyl-Sepharose column (Pharmacia) equilibrated with TSA. Some preparations were passed over a 1 ml protein A-Sepharose CL-4B column after diluting 1:1 with MAPS binding buffer (with 1% OG for LFA-3 from erythrocytes) (Biorad, Richmond, Calif.).

The LFA-3 purified as above has two forms: the mLFA-3 form, isolated from erythrocytes or lymphoblastoid cells, and the sLFA-3 form, isolated from lymphoblastoid cells. mLFA-3 has an intact phosphatidylinositol (PI) membrane anchor and is also referred to as the lipid linked form. sLFA-3 has had the PI membrane anchor cleaved by PIPLC. Of these two, only mLFA-3 can form micelles.

There is a third form of LFA-3, transmembrane LFA-3, or TM LFA-3, which does no- have a lipid membrane anchor but remains attached to the cell membrane by a transmembrane domain that is a part of the complete LFA-3 protein. TM LFA-3, like mLFA-3, can form micelles and will be described in more detail below First, sLFA-3 will be described.

Our recent finding that about half of the LFA-3 on the surface of B lymphoblastoid cells is attached to the membrane by a PI glycan moiety which is cleavable by PIPLC (Dustin, M.L., et al., Nature, 329:846 (1987)) allowed us to obtain a non-aggregated, i.e., non micelle-forming, form of LFA-3 for binding studies. LFA-3 released from the surface of live JY cells by PIPLC was purified by immunoaffinity chromatography, hydrophobic interaction chromatography on phenyl Sepharose, and protein A affinity chromatography. The middle step was added to remove traces of membranous material or LFA-3 micelles which might be released during enzyme treatment. The yield from 50 g of cells was about 100 μg. When this material was treated with N-glycanase, a single band of 25.5 kD was obtained which corresponds to the lipid-linked forms from JY cells and erythrocytes.

Figure 1:
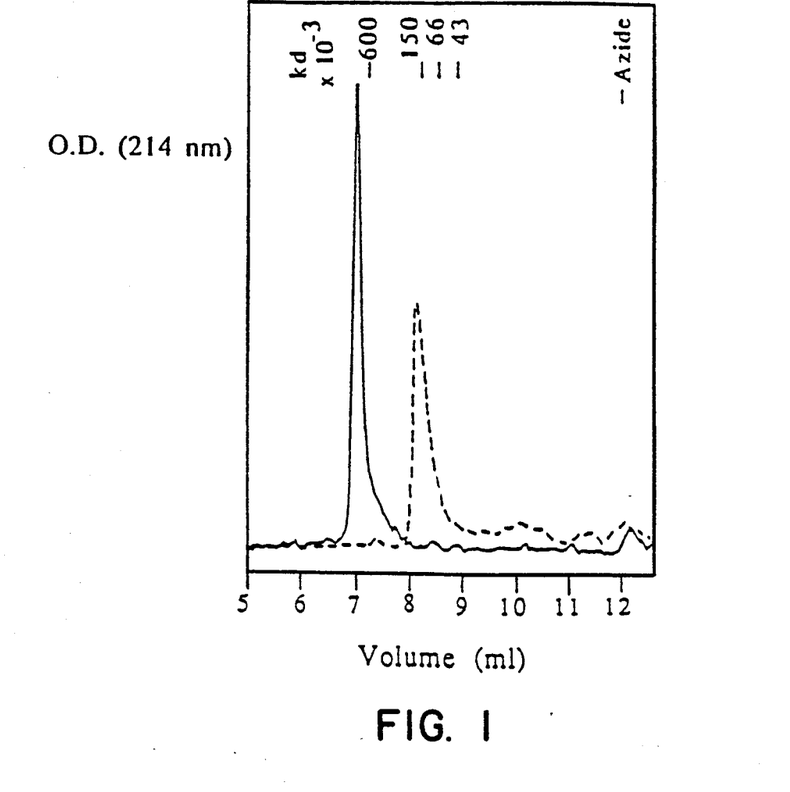
FIG. 1 is a graph depicting the results of gel filtration of two forms of LFA-3.

The structure of mLFA-3 in the form of micelles, as used in subsequent activation experiments, was studied by gel filtration. The results are shown graphically in FIG. 1. The size of mLFA-3 in the presence and absence of 1% OG detergent was examined by HPLC gel filtration. In the absence of detergent (solid line), mLFA-3 eluted slightly before thyroglobulin (600,000 kD) but after blue dextran on TSK GS 4000 or Zorbax GF 250 (Dupont) columns and had a diffusion coefficient similar to a globular protein of 700 kD. The dotted line shows the elution profile in the presence of 1% OG. In the presence of 1% OG all of the LFA-3 coeluted with IgG (150 kD). LFA-3 migrates at 55-70 kD in SDS-PAGE (Dustin, M. L.. et al., supra) The molecular weight of the mLFA-3 with and without detergent cannot be estimated without sedimentation data; however, these data show that mLFA-3 forms protein micelles of approximately 5 monomers or dimers in the absence of detergent. mLFA-3 does not form disulfide linked dimers based on SDS-PAGE, but the possibility that it forms non covalent dimers cannot be ruled out. Furthermore, sLFA-3 in the absence of detergent exists as a soluble molecule with a diffusion coefficient consistent with a monomer or dimer.

The second form of micelle-forming LFA-3 is the transmembrane form, TM LFA-3. The mRNA encoding this form differs from that of the mLFA-3 form, but only in the transmembrane and cytoplasmic domains of the molecule. The CD2 binding domain (the extracellular portion) of both forms of LFA-3 is identical.

Although TM LFA-3 has no lipid anchor, the cytoplasmic domain includes a hydrophobic amino acid sequence which remains attached to the purified protein. Micelle formation occurs by protein-protein interactions rather than lipid-lipid interactions but the result, micelle formation, is the same. TM LFA-3 and mLFA-3 micelles have comparable stability and target binding avidity.

It has been found that the TM form of LFA-3 occurs naturally in most nucleated cells, which often simultaneously also produce the lipid-linked form.

Formation of Micelles

Micelles of mLFA-3 and TM LFA-3 were prepared by three cycles of ultrafiltration using a Centricon 30 apparatus (Amicon, Danvers, Mass.), adding 2 ml of phosphate buffered saline (PBS) and reducing the volume to 50 μl with each cycle. Because the final ultrafiltrate of the last step contained the same low molecular weight components as the final retentate but not any LFA-3, this ultrafiltrate was used as a control for effects of buffer components in subsequent experiments.

Formation of LFA-3 micelles occurs spontaneously when detergent is removed or diluted below its critical micelle concentration. Detergent removal can be achieved by several techniques. The major requirement is that detergent is removed or diluted such that protein aggregation is the most favorable event rather than protein adsorption to other materials—i.e., test tube surfaces, etc. One technique which is successful with mLFA-3 is ultrafiltration in which an mLFA-3 solution in 1% octylglucoside detergent is concentrated from 2 ml to 50 μl and diluted with detergent-free solution. This results in dilution of octylglucoside to below its critical micelle concentration (25 mM). Other techniques for detergent removal/dilution include dialysis and sedimentation through detergent free sucrose gradients. The protein micelles generated by any technique will be functionally equivalent since the structure of the protein micelles is determined by the properties of the hydrophobic and hydrophilic portions of the protein and not on the means of detergent removal.

Whenever proteins with hydrophobic components, such as LFA-3, are purified, there is a tendency for these proteins to adhere to the lass or plastic containers used in the purification process. The rapid removal of the detergent counteracts this tendency, and promotes protein rather than protein plastic a protein-glass binding, and can result in approximately 100 percent recovery of the purified LFA-3 in micelle form. The micelles can be maintained in the PBS for at least two months without loss of activity. Theoretically, if the PBS is completely free of proteases, the storage life of micelles should be much longer.

Figures 2, 3:
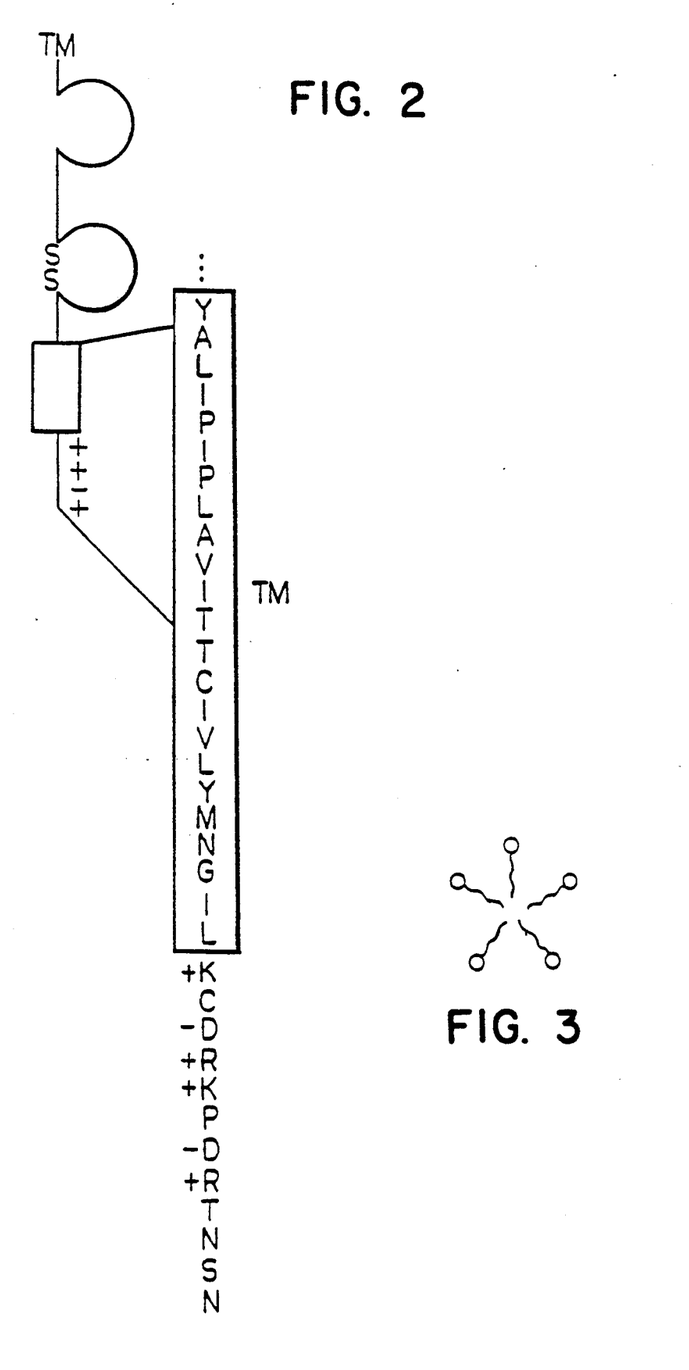
FIG. 2 is a schematic of the transmembrane (TM) form of LFA-3.
FIG. 3 is a schematic of an adhesion protein micelle.

Micelles created according to the invention have their hydrophobic lipid or hydrophobic proteinaceous "tails" sequestered within the micelle and the lobular hydrophilic domains at the perimeter facing outwards. FIG. 3 is a schematic of such a micelle containing five monomer units.

Formation of Micelles From Recombinant LFA-3

Micelles can also be formed from recombinantly produced LFA-3. The preferred method of producing recombinant LFA-3 is in a eukaryotic expression system that enzymatically attaches the PI anchor, e.g., Chinese Hamster Ovary (CHO) cells.

Figure 4:
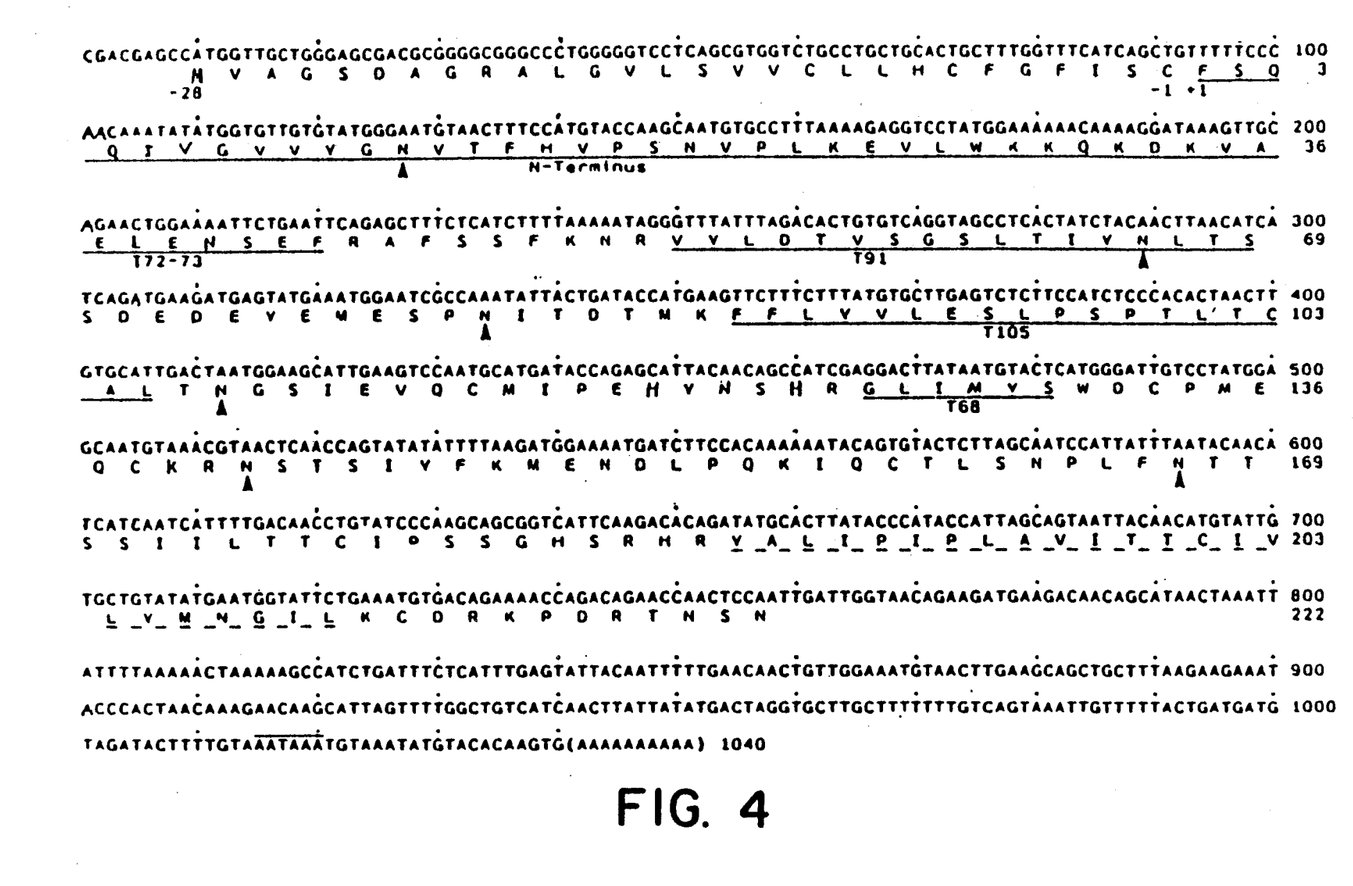
FIG. 4 is the DNA sequence and deduced amino acid sequence of human TM LFA-3 cDNA.

The DNA sequence for human TM LFA-3 cDNA and the deduced amino acid sequence are known (Wallner, B.P., et al., J. Exp. Med., 166:923-32 (1987)), and are given in FIG. 4 in which potential N-glycosylation sites are indicated by arrows and the potential transmembrane domain is underlined by a broken line. These sequence data are available from the EMBL/GenBank Data Libraries under accession number Y00636. The cDNA sequence for the PI form of LFA-3 is identical to that of the TM form except that it is slightly shorter. The cloned cDNA encoding the PI glycan linked form of LFA-3 is expressed in a CHO cell system by standard techniques. These cells recognize a transmembrane domain sequence and covalently bind the PI anchor to the remainder of the protein after translation. Alternatively, the TM form of LFA-3 can be produced in CHO cells or other cell systems that are not capable of attaching the PI anchor, such as murine L cells (Flavell et al. 1987).

The recombinant TM LFA-3 or mLFA-3 is isolated and caused to form micelles in the same manner as naturally occurring LFA-3, as described above.

Competition between LFA-3 Micelles and CD2 MAb.

A number of CD2 MAb's were tested for their ability to block binding of mLFA-3 to Jurkat cells or peripheral T-cells at saturating concentrations of MAb (Table 1). CD2 MAb's which strongly inhibit E-rosetting were able to completely block mLFA-3 binding.

MAbs used in this study are listed in Table 2. 9-1 was a gift of Dr. Dupont (Memorial Sloan-Kettering Cancer Institute, N.Y.). 9.6 was a gift of Dr. John Hansen (Fred Hutchinson Cancer Research Center, Seattle, Wash).

Binding of LFA-3 Micelles to Cell Surface CD2

It has been shown that iodinated LFA-3 binds to CD2 positive cells when Triton X 100 is absorbed with 15% bovine serum albumin, and that this binding is inhibited by CD2 Mab and LFA-3 MAb (Dustin, et al , supra) According to the present invention, mLFA-3 micelles were found to bind efficiently to Jurkat T leukemic cells or resting PBL-T (Table 3). mLFA-3 micelle binding was inhibited by the TS2/18 MAb, the LFA-3 MAb, and cold (unlabeled) mLFA-3 micelles.

Figure 5:
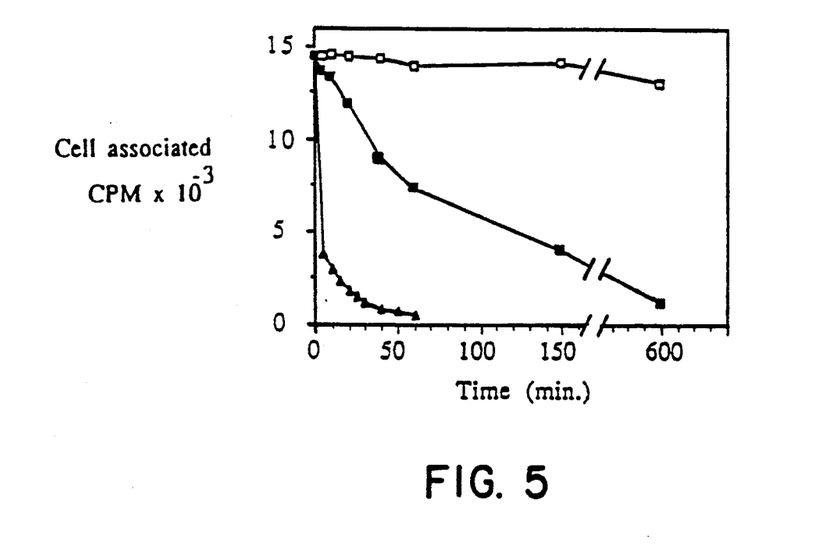
FIG. 5 is a graph of the dissociation time-course for LFA-3 micelles from Jurkat cells.

FIG. 5 is a graph of the dissociation time-course for mLFA-3 from Jurkat cells. When cells which had bound mLFA-3 micelles at 4° C. were resuspended in a large volume of medium containing no mLFA-3, the dissociation of bound mLFA-3 micelles was very slow ($t_{\frac{1}{2}} > 600$ min.; open squares), while in the presence of 10 $\mu$g/ml TS2/18 MAb (filled square) the dissociation rate was much more rapid ($t_{\frac{1}{2}} = 60$ min.,). When cells were resuspended in media containing 100 $\mu$g/ml TS2/18 MAb (filled triangle) the $t_{\frac{1}{2}}$ was less than 2 min. and dissociation was complete within 1 hour. Because TS2/18 MAb and mLFA-3 appear to bind CD2 in a strictly competitive manner, the increased rate of dissociation in the presence of CD2 MAb indicates that the mLFA-3 micelles bind multivalently to cell surface CD2.

The binding domains of these proteins in the micelles participate in multiple interactions when the micelle contacts the surface of a cell, thereby greatly increasing the avidity of the proteins for their targets. A single protein-target interaction has a tendency to rapidly dissociate whereas the micelle can cause up to approximately 5 to 10 such interactions to occur simultaneously. Thus the overall dissociation constant is greatly decreased for the micelle form of an adhesion protein due to this multivalent binding. To verify this, we compared the ability of mLFA-3 micelles and non-micelle sLFA-3 to bind to cell surface CD2. LFA-3 from JY cells and erythrocytes exhibit different degrees of glycosylation. Therefore, both mLFA-3 and sLFA-3 were isolated from JY cells to rule out differences in binding arising from differences in glycoslyation. mLFA-3 micelles from JY cells were of similar size to mLFA-3 micelles from erythrocytes despite being a mixture of PI and TM forms of LFA-3 (Dustin et al., Nature, supra). sLFA-3 was iodinated to the same specific activity as mLFA-3, and after incubation with Jurkat leukemic T-cells for 90 min at 4° C. cells were spun through an oil cushion. The level of JY mLFA-3 micelle binding was found to be 150 fold higher than JY sLFA-3 binding (Table 4). Consistent with this, cold sLFA-3 did not appreciably inhibit the binding of mLFA-3 to Jurkat cells when present at a 100 fold weight excess. Therefore, multivalency appears to be an important factor in high avidity mLFA-3 binding to cell surface CD2.

The complete reversal of mLFA-3 binding by CD2 MAb described above shows that LFA-3 is not endocytosed after 90 min. at 4° C. and that it is not inserting into membranes through its PI glycan anchor during this period. To further examine endocytosis of mLFA-3, LFA-3 was bound to Jurkat cells or PBL for 30 min. at 37° C. or 60 min. at 4° C. The cells were then washed with cold media and then incubated for 6 hrs. with 100 $\mu$g/ml TS2/18 MAb (Table 5). LFA-3 bound at 4° C. was almost completely released by TS2/18 MAb, but 50% of the Jurkat cells and 20% of the peripheral blood T lymphocytes (PBL-T) associated counts bound at 37° C. remained cell associated in the presence of TS2/18 MAb (Table 5) suggesting that this proportion of the LFA-3 was not on the cell surface, but had been internalized. When TS2/18 MAb was added with mLFA-3 at 37° C., no association of LFA-3 with the cells was detected, demonstrating that the persistent association is not due to non-specific lipid mediated insertion of mLFA-3 into the plasma membrane or to fluid phase pinocytosis.

The purified mLFA-3 was tested for binding to purified CD2 reconstituted into lipsomes bound to glass coverslips. Iodinated mLFA-3 micelles were found to bind to this solid phase (Table 6). The binding was inhibited by LFA-3 MAb and TS2/18 MAb, but not by the CD2.1 MAb, demonstrating that mLFA-3 binds to CD2 in the absence of other cell surface components.

Figure 6A:
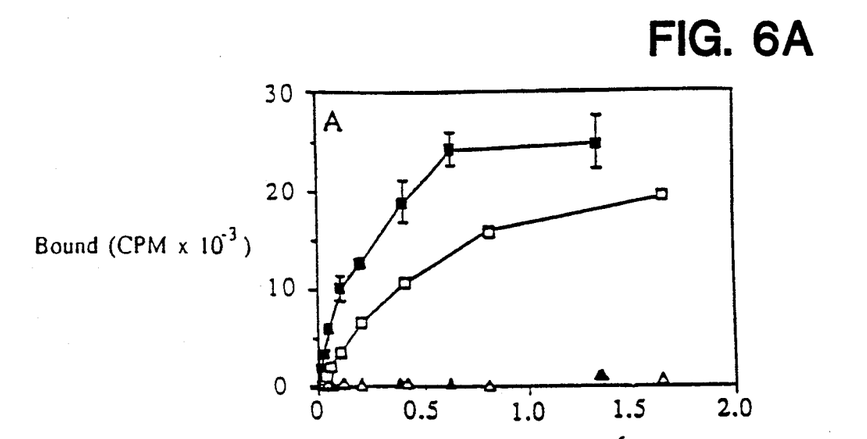
FIGS. 6a and 6b are graphs depicting equilibrium binding of LFA-3 micelles to Jurkat and resting T-cells and the same data analyzed by the Scatchard method, respectively.
Figure 6B:
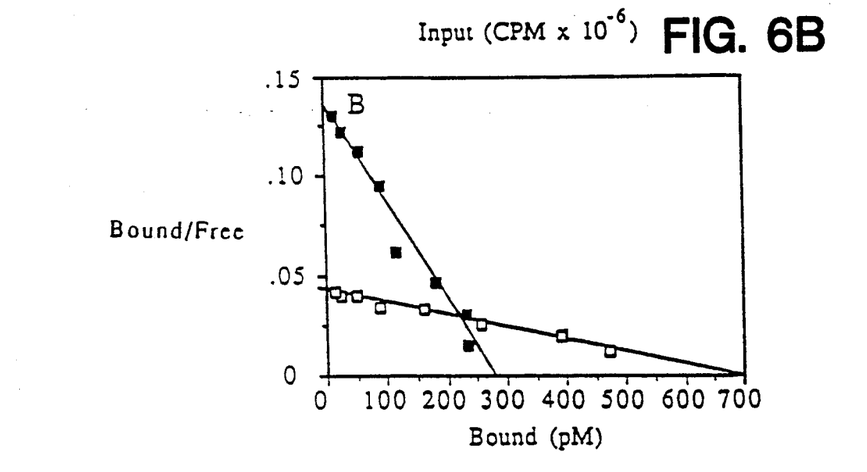

Equilibrium binding experiments were done to determine the number of mLFA-3 molecules bound per cell and the avidity of the interaction with CD2 on Jurkat cells and resting PBL-T cells. The results are shown graphically in FIGS. 6a and 6b. The percentage of active mLFA-3 protein micelles after iodination was determined by measuring the proportion of mLFA-3 which could be bound to three sequential aliquots of $10^7$ Jurkat cells. This was between 85 and 95% for different preparations. Specific mLFA-3 binding was defined as any binding inhibited by excess TS2/18 MAb. Binding of mLFA-3 was done for 1 hr. at 4° C. in the presence of control MAb (squares) or TS2/18 MAb (triangles). mLFA-3 bound saturably to Jurkat cells (filled symbols) and PBL-T (open symbols) (FIG. 6a). Scatchard plots showed that the $K_d$ for Jurkat CD2 was 1.7-2.2 nM, while the $K_d$ for PBL-T was 12-16 nM (FIG. 6b). This Kd value is a measure of the avidity of the LFA-3 micelles for each of these cell types. Approximately 420,000 mLFA-3 monomers bound per Jurkat cell, while about 50-80,000 mLFA-3 molecules bound to PBL-T measured at saturation These values are consistent with the relative numbers of CD2 molecules on Jurkat cells and PBL-T measured using equilibrium MAb binding (Martin, P.J., et al., J. Immunol., 131:180 (1983), Plunkett, M.L., et al., J. Immunol., 136:4181 (1986)). The presence of saturating concentrations of the non blocking CD2.1 MAb did not significantly affect either binding parameter for Jurkat cells or PBL-T.

Use of Micelles to Increase Proliferation of Cells mLFA-3 micelles alone have no effect on PBL-T proliferation, but they can induce proliferation of PBL-T in the presence of submitogenic concentrations of anti-CD2 MAb's. The combination of mLFA-3 micelles (40 nM) with CD2 MAb was found to be strongly mitogenic for peripheral blood mononuclear cells (PBMC) from all donors tested (Table 7). This response was usually (9 of 10 donors) seen in the absence of exogenous IL-2, although phorbol myristate acetate (PMA) was still required for a maximal response. Proliferation induced by the combination of mLFA-3 micelles and CD2.1 MAb was generally lower than that obtained with phytohemagglutanin (PHA), while the combination of mLFA-3, CD2.1 and PMA resulted in greater thymidine incorporation than PHA alone by up to two fold in some donors. The combination of mLFA-3 and CD2.1 MAb was also mitogenic for nylon wool enriched T-cells (Table 8).

The combination of sLFA-3 at concentrations up to 800 nM and CD2.1 MAb, with or without PMA, was not mitogenic for PBMC in two experiments for which sufficient amount of material could be obtained. Experiments with the same donors showed strong responses to mLFA-3 plus CD2.1 MAb with or without PMA.

Stimulation of proliferation by a combination of 9-1 and 9.6/35.1 MAbs was seen with nylon wool enriched PBL-T or PMBC in the presence of 15% human serum (Table 8). Under these conditions the combination of 9-1 MAb with 40 nM mLFA-3 was without effect except in one of two experiments done in round bottom wells with PBMC, in which case relatively weak stimulation augmented by exogenous IL 2 was seen (stimulation index = 16.8 vs 110 for 9-1+9.6 MAb's). With nylon wool enriched T-cells on flat bottom wells, mLFA-3 cooperated with 9-1 MAb only in the presence of 1 nM PMA. mLFA-3 appears to cooperate with 9 1 MAb for resting T cell activation under some conditions, but this activation is very weak compared to that achieved by a combination of mLFA-3 and CD2.1 MAb.

Figure 7A:
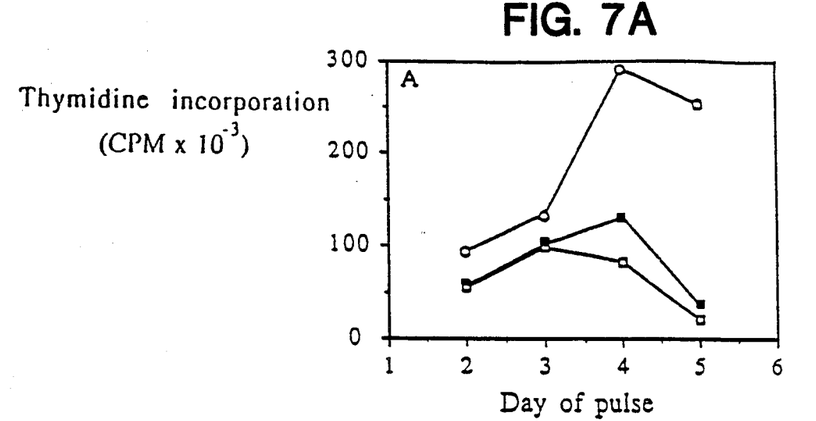
FIGS. 7a and 7b are graphs showing the time-course and dose-response for LFA-3 and CD2 monoclonal antibody (MAb)-induced proliferation.

Because the mLFA-3 with CD2.1 MAb response was stronger and more reproducible than the 9-1 MAb with mLFA-3 response, the former was further characterized. FIGS. 7a and 7b are graphs showing the time-course and dose-response for LFA-3 and CD2.1 MAb induced proliferation. PBMC were treated with mLFA-3 (40 nM) +CD2.1 10μg/ml) (open squares); mLFA-3, CD2.1, and IL-2 (filled squares); or mLFA-3, CD2.1, and PMA (open circles) from day zero until the 16 hour pulse was initiated on day 3. Stimulation of DNA synthesis by mLFA-3 and CD2.1 MAb peaked on days 3 to 4. (FIG. 7a). In the presence of exogenously added IL-2 and 1 nM PMA the optimal periods were days 3 to 4 and days 4 to 5, respectively.

Figure 7B:
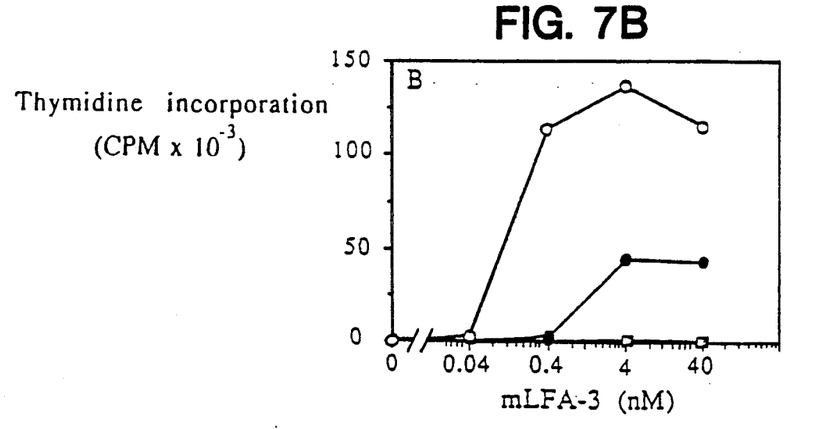

The dose-responses for mLFA-3 and CD2.1 MAb were determined in the presence of saturating concentrations of the other reagent. PBMC were treated with the indicated concentration of mLFA-3 with no addition (open squares), PMA (1 nM) (filled squares), CD2.1 (10μg/ml , or CD2.1 and PMA open circles). Wells were pulsed on day 3 for 16 hr. In the presence of saturating CD2.1 MAb (67 nM), maximal PBMC or PBL-T proliferation was obtained with 4 nM mLFA-3 (FIG. 7b). This is in the range of the $K_d$ for mLFA-3 binding to PBL-T of 12 nM. The presence of exogenous IL-2 did not alter the dose response, but, addition of 1 nM PMA decreased the mLFA-3 concentration required for maximal response 10 fold. Similarly, in the presence of 40 nM mLFA-3, the CD2.1 MAb concentration giving a maximal response was 6.7 nM, but only required for 0.67 nM in the presence of 1 nM PMA.

Inhibition of LFA-3 Dependent Activation

The proliferative response to mLFA-3 with CD2.1 MAb was completely blocked by both anti-LFA-3 MAb's and the 9.6 MAb. The 9.6 MAb blocks mLFA-3 binding to CD2 but is usually not comitogenic with CD2.1 MAb (Table 9). The response to mLFA-3 with CD2.1 MAb was also blocked by CD25 (anti-IL 2 receptor p55 chain) MAb suggesting that it is IL 2 dependent. The mitogenic response of PBMC or PBL-T to mLFA-3 with CD2.1 MAb was accompanied by aggregation of cells within 16 hours. These clusters could not have been the result of passive agglutination of cells by mLFA-3 micelles, because clusters were not seen with mLFA-3 in the absence of CD2.1 MAb.

Effect of LFA-3 Micelles on Intracellular Free $Ca^{+2}$

Figure 8:
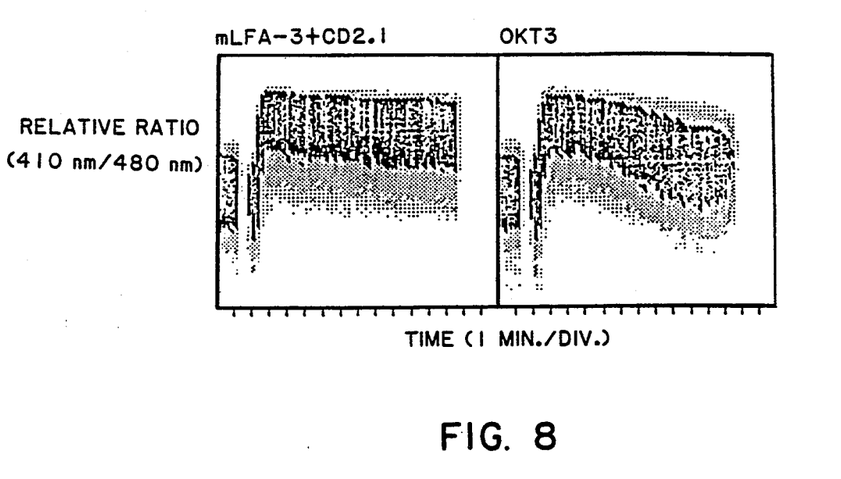
FIG. 8 is an emission spectra graph which shows the cytoplasmic mobilization of $Ca^{+2}$ over time in Jurkat cells induced by LFA-3 and CD2 MAb.
Figure 9:
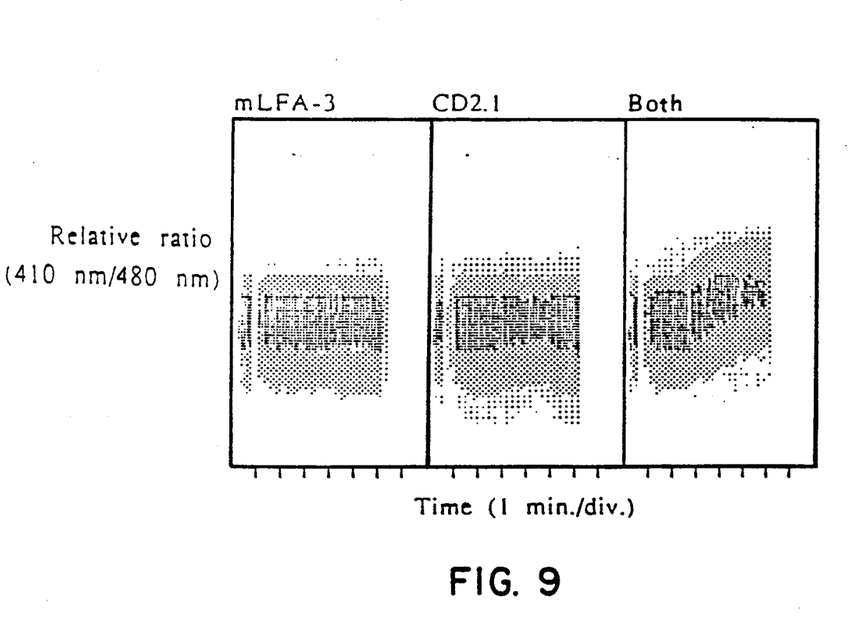
FIG. 9 is an emission spectra graph which shows the cytoplasmic mobilization of $Ca^+$ over time in resting T-cells induced by LFA-3 and CD2 MAb.

There are several early indicators of T cell activation useful in evaluating the activating potential of mLFA-3. Several studies have shown that combinations of CD2 MAb can stimulate $Ca^{+2}$ fluxes in T cell tumor lines. We have examined the ability of mLFA-3, alone and in combination with CD2.1 MAb, to stimulate $Ca^{+2}$ mobilization in Jurkat cells and PBL-T. Because $[CA^{+2}]_i$ responses can occur within minutes and can be measured on single cells, their detection demonstrates that the binding of the mLFA-3 micelles to cell surface CD2 leads to an activation signal without a chance for LFA-3 to insert into membranes or cross-link CD2 molecules on different cells. PBL-T or Jurkat cells were loaded with the fluorophore Indo-1 by incubation with its precursor, Indo 1 acetoxymethyl ester, and relative $[Ca^{+2}]_i$ was determined by flow microfluorimetry using the ratio of Indo-1 emissions at different wavelengths (410 nm/480 nm) as an indication of $[Ca^{+2}]_i$. When mLFA-3 (up to 240 nM) was added to Jurkat cells (at 30–60 sec.) there was no change in the ratio within 15 min. (FIG. 9). Similarly, CD2.1 MAb (67 nM) along had no effect on $[Ca^{+2}]_i$ (FIG. 9). However, when mLFA-3 and CD2.1 MAb were added simultaneously, there was a rapid and sustained increase in $[Ca^{+2}]_i$ (FIG. 9) which was similar in magnitude to that seen with CD3 e.g., OKT3 (FIG. 8). Similar results were obtained with PBL-T using 120 nM mLFA-3. There was no evidence of cell cell interaction during these experiments, as there was no change in forward angle light scatter.

Figure 10A:
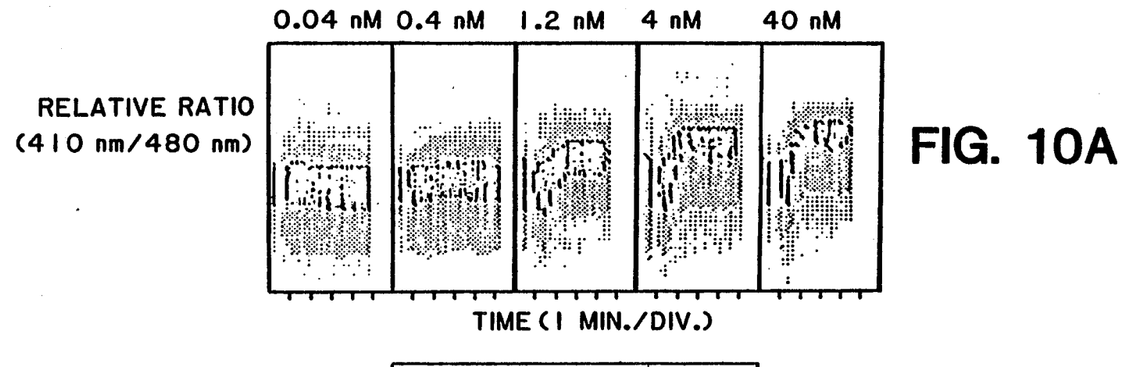
FIGS. 10a and 10b are an emission spectra graph and a set of histograms, respectively, that show the concentration dependence of $Ca^+$ influx increase in Jurkat cells on the LFA-3 occupation of CD2.
Figure 10B:
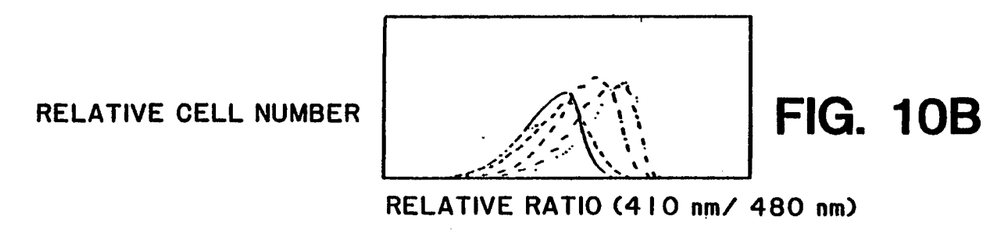

To allow direct comparison of $Ca^{+2}$ mobilization to equilibrium mLFA-3 binding data, Jurkat cells were equilibrated with different concentrations of mLFA-3 by incubation for 30 min at 37° C., and then CD2.1 MAb was added to initiate $[Ca^{+2}]_i$ mobilization (FIG. 10). Under these conditions, a near half-maximal increase in $[Ca^{+2}]_i$ was seen at about 1.2 nM mLFA-3, which is very close to the $K_d$ for mLFA 3 binding to Jurkat CD2 determined as described above. The addition of ionomycin to Jurkat cells after 240 nM mLFA-3 and CD2.1 resulted in a further increase in $[Ca^{+2}]_i$, suggesting that the Indo-1 was not at saturation for $Ca^{+2}$ in these experiments. Therefore, it appears that the signal delivered through CD2 by a combination of mLFA-3 and CD2.1 which leads to an increase in $[Ca^{+2}]_i$ is proportional to the degree of saturation of CD2 with mLFA-3. FIG. 10b is a graph showing histograms of sections through activation time plots at 3 minutes: 0.04 nM (solid line), 0.4 nM (dashed line), 1.2 nM (dot-dash line), 4 nM (dot-dot-dash line) and 40 nM (dotted line).

Use of Adhesion Protein Michelles in Therapy

Protein micelles of the invention can be used therapeutically to competitively inhibit reactivity of specific surface antigens on target molecules. In particular, LFA-3 michelles bind to cell surface DC2 on T-lymphocytes with high avidity, rendering them therapeutically useful by inhibiting binding of the T-lymphocytes to other cells.

Furthermore, LFA-3 micells can be coionternalized with CD2, causing loss of CD2 from the cell surface. This irreversible internalization allows LFA-3 micells to be used therapeutically below the Kd of monomeric LFA-3 Kd to down-regulate CD2.

LFA-3 micells of the invention in a physiologically compatible carrier such as saline, are preferably administered to yield a therapeutically effective concentration of LFA-3 in the blood of 0.04 to 4 nM. Depending upon blood volume of the patient and clearance of the micells from the bloodstream, 0.5 to 50 μg/kg of micelle/patient/day are administered intravenously to achieve this concentration. The micelles function by effectively saturating CD2 receptor sites on the surfaces of T-cells and thereby inhibit binding of those T-cells to other cells. This binding inhibition can ameliorate rate the effects of disease states in which binding of T-cells to other cells is a continuing factor, e.g., autoimmune diseases such as rheumatoid arthritis; allograft rejection; and graft versus-host disease.

Other embodiments are within the following claims.

TABLE 1

| Inhibition of mLFA-3 binding by CD2 MAb | |
|---|---|
| Cold ligand | $^{125}$I-mLFA-3 bound/$10^6$ cells (CPM) |
| control MAb | 20,531 ±596 |
| 9.6 | 173 ±17 |
| TS2/18 | 153 ±57 |
| 9-2 | 154 ±8 |
| CD2.8 | 173 ±29 |
| 35.1 | 7,171 ±98 |
| CD2.9 | 164 ±50 |
| CD2.1 | 22,817 ±362 |
| 9-1 | 24,092 ±878 |
| D66 | 16,073 ±72 |
| OKT3 | 21,342 ±487 |

Binding to Jurkat cells was done for 1 hr. at 4° C. Input counts were 100,000/$10^6$ cells. Bound and free were separated by centrifugation through a 15% BSA cushion. All the MAb except control and OKT3 are against CD2. Results are average of quadruplicates with standard deviation and are representative of two experiments.

TABLE 2

| MAb | Specificity | Isotype | Form | Reference |
|---|---|---|---|---|
| TS2/18 | CD2 | mouse IgG1 | purified | 1 |
| 9-1 | CD2 | mouse igG3 | purified | 3 |
| CD2.1 | CD2 | mouse IgG1 | purified or ascites | 2 |
| CD2.8 | CD2 | rat IgG2a | ascites | 2 |
| CD2.9 | CD2 | rat IgG2a | ascites | 2 |
| 9.6 | CD2 | mouse IgG2a | ascites | 4 |
| D66 | CD2 | mouse IgG2b | ascites | 5 |
| 9.2 | CD2 | mouse IgM | ascites | 6 |
| 35.1 | CD2 | mouse IgG2a | ascites | 7 |
| TS1/18 | LFA-1β | mouse IgG1 | ascites | 1 |
| TS2/9 | LFA-3 | mouse IgG1 | purified | 1 |
| OKT3 | CD3 | mouse IgG2a | culture sup | 8 |

1. Sanchez-Madrid, F., et al., Proc. Natl. Acad. Sci. USA, 79:7489 (1982).
2. Olive D., et al., Euro. J. Immunol., 16:1063 (1986).
3. Bernard A., et al., Human Immunology, 17:388 (1986).
4. Kamoun M., et al., J. Exp. Med., 153:207 (1981).
5. Bernard A., et al., J. Exp. Med., 155:1317 (1982).
6. Bernard A., et al., Summary of the CD2 Workshop: In Leukocyte typing III, (A. J. McMichael, ed., Oxford Univ. Press, Oxford, p. 106 (1987)).
7. Martin P. J., et al., J. Immunol., 131:180 (1983).
8. Chang, T. W., et al., Proc. Nat. Acad. Sci. USA, 78:1805 (1981).

TABLE 3

Binding of $^{125}$I-mLFA-3 to Jurkat cells and resting T cells.

| Cold ligands | $^{125}$ I-mLFA-3 bound/ 10$^6$ cells (CPM) | |
|---|---|---|
| | Jurkat Cells | resting T cells |
| control MAb | 82,513 | 33,262 |
| mLFA-3 | 4,414 | 1,152 |
| TS2/18 CD2 MAb | 440 | 93 |
| TS2/9 LFA-3 MAb | 510 | 192 |

Binding was done for 1 hr. at 4° C. Input 125 I-mLFA-3 was 200,000 cpm. Bound and free radioactivity were separated by centriguation through a 15% BSA cushion. Control IgGl, TS2/18 and TS2/9 were added at 10 µg/ml and cold mLFA-3 was added at 5 µg/ml. Results are averages of duplicates and are representative of three experiments.

TABLE 4

Binding of PIPLC released LFA-3 to Jurkat

| Additions | sLFA-3 | mLFA-3 |
|---|---|---|
| control MAb | 5,553 ± 387 | 148,760 ± 4003 |
| TS2/18 | 4,030 ± 14 | 5,023 ± 23 |

Jurkat cells (10$^6$) were incubated with 500,000 CRM of either sLFA-3 or mLFA-3, both prepared from JY cells, for 2 hrs. at 4° C. and aliquots were centrifuged through oil cushions.

TABLE 5

Accessibility of bound mLFA-3 to extracellular TS2/18

| Additions | | Cell Associated CPM | |
|---|---|---|---|
| Pre-incubation | Post incubation | Jurkat | PBL-T |
| 4° C. control | control | 11,441 ± 500 | 1,543 ± 225 |
| TS2/18 | control | 86 ± 5 | 95 ± 14 |
| control | TS2/18 | 299 ± 26 | 111 ± 13 |
| 37° C. control | control | 10,990 ± 941 | 1,326 ± 86 |
| TS2/18 | control | 67 ± 12 | 89 ± 19 |
| control | TS2/18 | 4,975 ± 400 | 390 ± 43 |

Jurkat cells of PBL-T (5×10$^5$) were incubated with 125 I-mLFA-3 (100,000 CPM) for 60 min. at 4° C. or 30 min. at 37° C. Jurkat cell and PBL-T CD2 was initially at approximately 10% occupation with LFA-3. The post-incubation at 4° C. without or with TS2/18 was carried out for 6 hrs. to insure complete dissociation of accessible LFA-3. Data are means of quadruplicate determinations with standard deviations.

TABLE 6

Binding of mLFA-3 to purified CD2 in plastic bound vesicles

| Cold ligand | $^{125}$I-mLFA-3 bound/well |
|---|---|
| control MAb | 8,040 |
| TS2/18 MAb | 35 |
| CD2.1 MAb | 8,122 |
| TS2.9MAb | 612 |

Input counts were 50,000. Bound and free were separated by five washes over 15 min. Results are averages of duplicates and are representative of results obtained in three experiments.

TABLE 7

Induction of T cell proliferation by mLFA-3 and CD2.1

| Additions | $^3$H-thymidine incorporation/ 5 × 10$^4$ PBMC (CPM) | | |
|---|---|---|---|
| | Exp. 1 | Exp. 2 | Exp. 3 |
| buffer | 593 | 392 | 417 |

TABLE 7-continued

Induction of T cell proliferation by mLFA-3 and CD2.1

| Additions | $^3$H-thymidine incorporation/ 5 × 10$^4$ PBMC (CPM) | | |
|---|---|---|---|
| | Exp. 1 | Exp. 2 | Exp. 3 |
| mLFA-3 | 411 | 645 | 549 |
| CD2.1 | 437 | 839 | 646 |
| IL-2 | 1,451 | 2,145 | 1,034 |
| mLFA-3 + IL-2 | 1,345 | 1,399 | 1,284 |
| CD2.1 + IL-2 | 1,609 | 2,039 | 1,545 |
| PMA | 1,713 | 1,382 | 834 |
| mLFA-3 + PMA | 1,549 | 978 | 828 |
| CD2.1 + PMA | 1,704 | 1,252 | 1,009 |
| mLFA-3 + CD2.1 | 22,294 | 35,439 | 47,478 |
| mLFA-3 + CD2.1 + IL-2 | 22,497 | 37,065 | 45,384 |
| mLFA-3 + CD2.1 + PMA | 77,784 | 114,313 | 153,240 |

Additions were as indicated on day zero: rIL-2 (o.lng/ml), PMA (1nM), CD2.1 (1:500 dilution of ascites or 10 µg/ml), and mLFA-3 (40nM). PHA (1 µg/ml) gave approximately 80,000–100,000 cpm on day 3 to 4 in these experiments. Wells were pulsed with [$^3$H]-thymidine on day 3 for 16 hr. Results are means of triplicates and are representative of 14 experiments.

TABLE 8

Induction of T cell proliferation by mLFA-3 and 9-1

| Additions | $^3$H-thymidine incorporation/ 5 × 10$^4$ cells(CPM) | |
|---|---|---|
| | PBMC | T cells |
| buffer | 2,029 | 262 |
| CD2.1 | 3,066 | 565 |
| 9-1 | 2,045 | 510 |
| mLFA-3 | 1,145 | 342 |
| CD2.1 + PMA | 4,748 | 1,159 |
| 9-1 + PMA | — | 10,520 |
| mLFA-3 + PMA | 2,463 | 2,052 |
| CD2.1 + mLGA 3 | 263,326 | 21,476 |
| CD2.1 + mLFA-3 + PMA | 330,866 | 216,933 |
| 9-1 + IL-2 | *4,078 | — |
| 9-1 + mLFA-3 | *7,193 | 1,074 |
| 9-1 + mLFA-3 + PMA | — | 77,582 |
| 9-1 + mLFA-3 + IL-2 | *34,074 | — |
| 9-1 + 9.6 | *181,570 | 40,764 |

PBMC and nylon wool enriched T-cells were from different donors. Experiments with PBMC was done in the presence of 15% the inactivated human serum. Points with (*) were done in round bottom wells. Corresponding conditions in flat wells gave lower stimulation. Additions were made on day zero and wells were pulsed on day 3 for 16 hr. 9-1 MAb was added at 1 µg/ml; 9.6 MAb at 1:0000 dilution of ascites. Other concentrations as in Table 4. Results are means of triplicate determinations and are representative of two experiments.

TABLE 9

Inhibition of proliferation by MAb to LFA-3, CD2 and LFA-1

| Additions | $^3$H-thymidine incorporation/5 × 10$^4$ cells(CPM) | |
|---|---|---|
| | CD2.1 + LFA-3 | CD2.1 + mLFA-3 + PMA |
| control MAb | 35,439 | 114,313 |
| TS2/9 | 1,684 | 1,116 |
| 9.6* | 776 | 6,375ᶜ |

PBMC were used. All additions were made on day zero and wells were pulsed on day 3 for 16 hrs. *9.6+CD2.1 gave 549 cpm and 9.6+CD2.1+PMA gave 1663 cpm with this donor. TS2/9 MAb wad added at 10 µg/ml. 9.6 was added at 1:5000 dilution of ascites. All results are means of triplicate determinations from a single experiment and are representative of three experiments.

We claim:

1. A micelle of a purified adhesion protein which naturally includes a phosphatidylinositol lipid anchor, said micelle being capable of binding multivalently to a plurality of target molecules on a cell surface.

2. The micelle of claim 1, comprising about five to ten molecules of said protein.

3. The micelle of claim 1, wherein said adhesion protein is mLFA-3.

4. The micelle of claim 1, wherein said adhesion protein is synthesized by recombinant DNA techniques.

5. The micelle of claim 1, wherein said micelle is about 200 angstroms in diameter.

6. A purified adhesion protein micelle, said adhesion protein occurring naturally on the surface of a cell and naturally having a phosphadidylinositol lipid anchor, said micelle being capable of binding multivalently to a plurality of target molecules on a cell surface.

* * * * *

UNITED STATES PATENT AND TRADEMARK OFFICE
CERTIFICATE OF CORRECTION

PATENT NO. : 5,071,964  
DATED : December 10, 1991  
INVENTOR(S) : Michael Dustin, et al Page 1 of 4

It is certified that error appears in the above-indentified patent and that said Letters Patent is hereby corrected as shown below:

On the title page, item [63] and in col. 1, line 7, "Feb. 26, 1988" should read --Feb. 26, 1987--.

Item [56], "References Cited", "(Wallner et al.)", "Glcoprotein" should read --Glycoprotein--.

Column 1, lines 39-40, "MORE PREFERABLY" should be --more preferably--.

Column 1, line 41, delete "more preferably <20 nM".

Column 2, lines 2-3, "ery.thmatosis" should be --erythmatosis--.

Column 2, line 15, "alphipathic" should be --amphipathic--.

Column 2, lines 18-19, "a polar" should be --apolar--.

Column 2, line 54, "$Ca^+$" should be --$Ca^{+2}$--.

Column 2, line 58, "$Ca^+$" should be --$Ca^{+2}$--.

Column 3, line 11, "65.677" should be --165:677--.

UNITED STATES PATENT AND TRADEMARK OFFICE
CERTIFICATE OF CORRECTION

PATENT NO. : 5,071,964
DATED : December 10, 1991
INVENTOR(S) : Michael Dustin, et al It is certified that error appears in the above-indentified patent and that said Letters Patent is hereby corrected as shown below:

Column 3, line 22, "$^3$H phos" should be --$^3$H-phos--.

Column 3, line 45, "lipid linked" should be --lipid-linked--.

Column 3, line 49, "no-" should be --not--.

Column 3, line 54, after "below" insert a period.

Column 4, line 24, "non covalent" should be --non-covalent--.

Column 5, line 10, "lass" should be --glass--.

Column 5, line 13, "protein" (first occurrence) should be --protein-protein--.

Column 5, line 13, "protein plastic a" should be --protein-plastic and--.

Column 5, line 23, "lobular" should be --globular--.

Column 7, line 40, after "saturation" insert a period.

Column 7, line 46, "non blocking" should be --non-blocking--.

Column 7, line 55, "CD2" should be --CD2.1--.

UNITED STATES PATENT AND TRADEMARK OFFICE
CERTIFICATE OF CORRECTION

PATENT NO. : 5,071,964   Page 3 of 4
DATED : December 10, 1991
INVENTOR(S) : Michael Dustin, et al It is certified that error appears in the above-indentified patent and that said Letters Patent is hereby corrected as shown below:

Column 8, line 18, "9 1" should be --9-1--.

Column 8, line 42, after "ml" insert --)--.

Column 8, line 42, before "open" insert --(--.

Column 9, line 23, "along" should be --alone--.

Column 9, line 30, "cell cell" should be --cell-cell--.

Column 9, line 39, "mLFA3" should be --mLFA-3--.

Column 9, line 54, "Michelles" should be --Micelles--.

Column 9, line 58, "michelles" should be --micelles--.

Column 9, line 62, "micells" should be --micelles--.

Column 9, line 62, "coionternalized" should be --co-internalized--.

Column 9, line 64, "micells" should be --micelles--.

Column 9, line 67, "micells" should be --micelles--.

Column 10, line 3, "micells" should be --micelles--.

UNITED STATES PATENT AND TRADEMARK OFFICE
CERTIFICATE OF CORRECTION

PATENT NO. : 5,071,964
DATED : December 10, 1991
INVENTOR(S) : Michael Dustin, et al It is certified that error appears in the above-indentified patent and that said Letters Patent is hereby corrected as shown below:

Column 10, line 13, "graph versus-host" should be --graft-versus-host--.

Col. 10, in Table 2, column 3, line 2, "igG3" should be --IgG3--.

Column 11, line 26, "CRM" should be --CPM--.

Column 12, line 66, "wad" should be --was--.

Signed and Sealed this

Fourteenth Day of September, 1993

*Attest:*

BRUCE LEHMAN

*Attesting Officer      Commissioner of Patents and Trademarks*

UNITED STATES PATENT AND TRADEMARK OFFICE
CERTIFICATE OF CORRECTION

PATENT NO.    : 5,071,964

DATED         : December 10, 1991

INVENTOR(S)   : Michael Dustin and Timothy Springer

It is certified that error appears in the above-identified patent and that said Letters Patent is hereby corrected as shown below:

Column 1, line 5, insert  --This invention was made with government support under Grant No. CA 31799 awarded by the National Institutes of Health. The government has certain rights in the invention.--

Signed and Sealed this

Thirteenth Day of December, 1994

Attest:

BRUCE LEHMAN

Attesting Officer

Commissioner of Patents and Trademarks